United States Patent [19]

Mori et al.

[11] Patent Number: 4,868,747
[45] Date of Patent: Sep. 19, 1989

[54] METHOD AND SYSTEM FOR DYNAMIC COMPUTED TOMOGRAPHY SCANNING AT CYCLIC DISPLACEMENT POINTS

[75] Inventors: Issei Mori, Tochigi; Tadatoki Yoshida, Otawara, both of Japan

[73] Assignee: Kabushiki Kaisha Toshiba, Kanagawa, Japan

[21] Appl. No.: 84,170

[22] Filed: Aug. 12, 1987

[30] Foreign Application Priority Data

Aug. 12, 1986 [JP] Japan ................................ 61-189173

[51] Int. Cl.$^4$ ............................................. G06F 15/42
[52] U.S. Cl. ........................... 364/413.18; 364/413.16; 364/413.19; 382/6; 378/901
[58] Field of Search .............. 364/414, 413.16, 413.18, 364/413.19; 378/90, 97, 99, 901; 382/6, 52, 54; 128/630

[56] References Cited

U.S. PATENT DOCUMENTS

| | | | |
|---|---|---|---|
| 4,037,585 | 7/1977 | Gildenberg | 378/8 |
| 4,182,311 | 1/1980 | Seppi et al. | 128/653 |
| 4,685,146 | 8/1987 | Fenster et al. | 382/54 |
| 4,703,424 | 10/1989 | Gullberg | 364/414 |
| 4,729,099 | 3/1988 | Iverson et al. | 364/414 |

Primary Examiner—A. D. Pellinen
Assistant Examiner—Jeffrey A. Gaffin
Attorney, Agent, or Firm—Finnegan, Henderson, Farabow, Garrett, & Dunner

[57] ABSTRACT

A computed tomography method and system for performing dynamic scans of objects undergoing cyclic displacement, for example a human heart. Characteristic curves are generated from images reconstructed from projection data synchronized with the cyclic displacement of the object. Each image reflects one displacement cycle of the object, and consists of projection data collected, in one case, within a phase window centered on a specified phase of cyclic displacement of the object, and in another case, consists of projection data collected between two specified phases of cyclic displacement.

8 Claims, 8 Drawing Sheets

| SOURCE POSITION t = | PROJECTION NUMBER | PHASE OF WAVE "R" ∅ = (+) (−) | EKG |
|---|---|---|---|
| 1 | (1) | 1 , −141 | |
| 2 | (2) | 2 , −140 | |
| 3 | (3) | 3 , −139 | |
| ⋮ | ⋮ | ⋮ | P |
| 136 | (136) | 136 , −6 | |
| 137 | (137) | 137 , −5 | |
| 138 | (138) | 138 , −4 | |
| 139 | (139) | 139 , −3 | |
| 140 | (140) | 140 , −2 | Q |
| 141 | (141) | 141 , −1 | |
| 142 | (142) | 0 , 0 | R |
| 143 | (143) | 1 , −348 | |
| 144 | (144) | 2 , −347 | S |
| ⋮ | ⋮ | ⋮ | |
| 490 | (490) | 348 , −1 | |
| 491 | (491) | 0 , 0 | R |
| 492 | (492) | 1 , −372 | |
| 493 | (493) | 2 , −371 | |
| 494 | (494) | 3 , −370 | S |

( SAMPLE PHASE WINDOW )

| SLICE NO. | PROJECTION NO. | | PHASE ∅ OF "R" WAVE | |
|---|---|---|---|---|
| | | | ∅1 | ∅2 |
| 1 | (2) | ~ (282) | −140 | ~ 140 |
| 2 | (351) | ~ (631) | −140 | ~ 140 |
| 3 | (722) | ~ (1002) | −140 | ~ 140 |
| 4 | (991) | ~ (1271) | −140 | ~ 140 |
| 5 | (1306) | ~ (1586) | −140 | ~ 140 |
| 6 | (1674) | ~ (1954) | −140 | ~ 140 |
| ⋮ | ⋮ | ⋮ | ⋮ | ⋮ |
| 15 | (4757) | ~ (5037) | −140 | ~ 140 |

PHASE OF WAVE "R" TO "R" PEAK

| SLICE NO. | PROJECTION NO. | | |
|---|---|---|---|
| 1 | (142) | ~ | (490) |
| 2 | (491) | ~ | (771) |
| 3 | (862) | ~ | (1142) |
| 4 | (1131) | ~ | (1411) |
| 5 | (1446) | ~ | (1726) |
| 6 | (1814) | ~ | (2094) |
| ⋮ | | | |
| 15 | (4897) | ~ | (5177) |

METHOD AND SYSTEM FOR DYNAMIC COMPUTED TOMOGRAPHY SCANNING AT CYCLIC DISPLACEMENT POINTS

FIELD OF THE INVENTION

This invention relates generally to a medical diagnostic apparatus and method for performing Computed Tomography (CT) dynamic studies of a moving object.

BACKGROUND INFORMATION

Non-invasive methods of measuring blood flow in human body organs typically involve injection or inhalation of a contrast medium, followed by generation of a series of CT images from an X-ray CT device to measure the concentration of the contrast medium in a part of the organ of interest, such as the brain. This method is described by Teeter and Colsher in "Imaging of Xenon Enhanced Cerebral Blood Flow with High Resolution CT," Radiology, Oct. 1984. An improved dynamic scanning apparatus and method for measuring the rate of build-up of the concentration of the contrast medium is described in U.S. Pat. No. 4,718,432, entitled "CT Imaging Apparatus and Method for Measuring Local Cerebral Blood Flow" by Kimura et al, assigned to the same assignee.

Generally a characteristic curve of the relative absorption of X-rays, called the CT number, is made for a region of interest (ROI) over a period of time by making multiple images. The resulting curve, an example of which is shown in FIG. 8, provides a basis to calculate the blood flow in the ROI. This technique most accurately is applied to stationary organs because motion of the ROI, such as from the beating of the heart or from respiratory movement, causes changes in contrast resulting in errors in the characteristic curve. Images and characteristic CT curves built up from several data points using standard dynamic scanning methods while the ROI is in motion result in dynamic curves unacceptable for diagnosis.

To perform an accurate dynamic scan, the collected data must be synchronized with the motion of the ROI to properly average the motion affects so that each CT number plotted is consistent with the other CT numbers.

SUMMARY OF THE INVENTION

It is therefore an object of this invention to provide an accurate method and apparatus for performing dynamic scans of objects moving cyclicly.

Another object of this invention is to permit nonintrusive examination of blood quantity and/or blood velocity flow in arteries or veins in a moving object such as a heart or lung using CT techniques.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

To achieve the foregoing objects and in accordance with the purposes of the invention as embodied and broadly described herein, a Computed Tomographic system is provided enabling dynamic scanning of an object at cyclic displacements while exposing radiation energy to the object comprising: scanning means for generating projection data from the object by scanning a portion of the object over a selected time period; detecting means for generating displacement signals responsive to cyclic displacement of the object during the time period; memory means coupled to the scanning means and the detecting means for correlating with respect to time and storing the projection data and the displacement signals; first selecting means coupled to the memory means for selecting specific phases of cyclic displacement in a region scanned within the object; reconstructing means coupled to the first selecting means and the memory means for generating a plurality of images of the object from the projection data generated between the specific phases of the displacement signals, each of the images being generated from one displacement cycle of the object; second selecting means coupled to the reconstructing means for selecting a region of interest in the region scanned within the object; and dynamic curve display means coupled to the reconstructing means to average the CT number within the region of interest for each of the images and to display a dynamic curve of the averaged CT numbers as a function of time.

The accompanying drawings, which are incorporated in and constitute a part of the specification, illustrate a preferred embodiment of the invention and, together with the general description given above and the detailed description of the preferred embodiments given below, serve to explain the principles of the invention.

BRIEF DESCRIPTION OF THE DRAWINGS

FIG. 3 is a table and graph illustrating the relationship of the projection number and the phase of the EKG R wave according to the present invention.

DESCRIPTION OF THE PREFERRED EMBODIMENT

Reference will now be made in detail to the present preferred embodiment of the invention as illustrated in the accompanying drawings. Identical reference numbers designate identical or corresponding parts throughout the several views of the figures.

Reference is now made to FIG. 1 of the drawings, which illustrates a system for dynamic scanning at cyclic displacement points using an X-ray scanning apparatus, for example, a fourth generation Computed Tomography (CT) system.

Figure 1A:
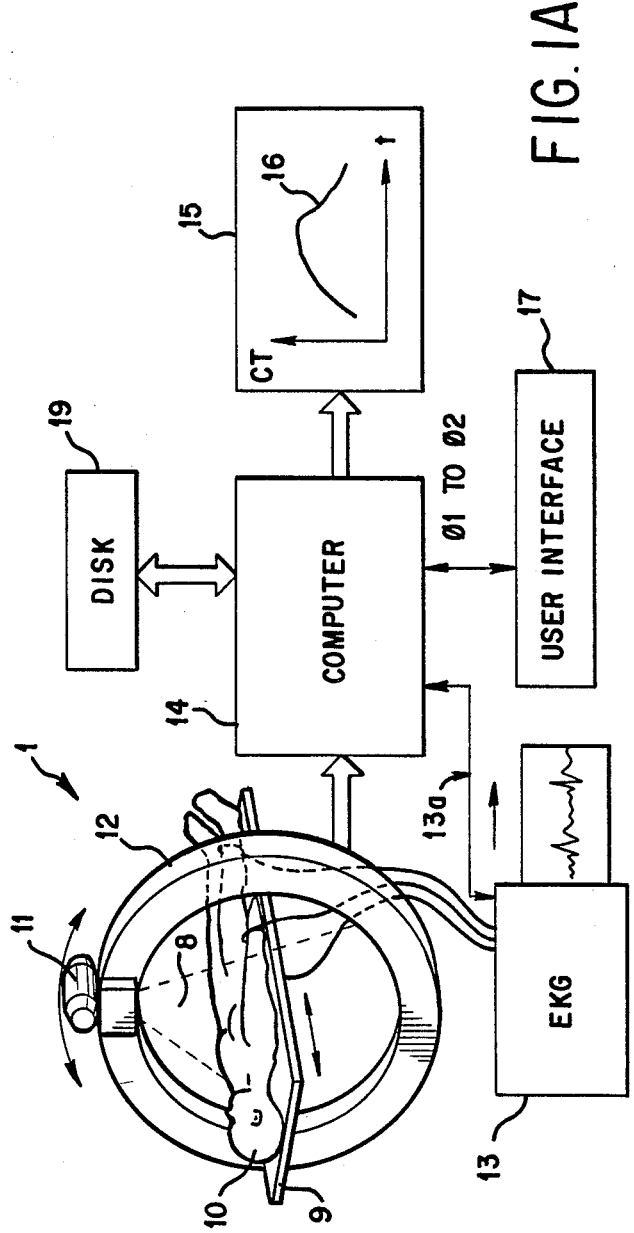
FIG. 1A is a schematic block diagram illustrating the dynamic scan system according to the present invention.

FIG. 1A shows a simplified external perspective view of scanning system 1 that generates projection data to be used by the present invention for generating images and dynamic scans of an object, for example portions of a patient.

System 1 of FIG. 1A shows a fourth generation CT device which comprises generally a couch 9 being movable along an axis running from the head to the feet of patient 10, radiation source 11 comprising an X-ray source capable of projecting an X-ray pattern in the form of fan beam 8 rotating continuously around patient 10, an X-ray detector 12 in a ring centered on the axis of rotation of the X-ray source 11 to detect X-rays passing through patient 10 and for generating projection data.

The signals from the X-ray detector 12 which are converted into radiation intensity signals are sent to computer 14, and are then reconstructed to create a CT number, CT tomogram, and dynamic curve 16.

The basic system and method of a CT apparatus such as the one shown in FIG. 1A is disclosed in detail, for example, in U.S. Pat. No. 4,206,362 and U.S. Pat. No. 4,075,492.

Cardiac computed tomography combines an electrocardiograph 13 with the CT scanner. The detecting means for generating displacement signals responsive to cyclic displacement of a patient's heart during the time period that projection data are collected consists of the electrocardiograph 13 which detects electrical movement of the patient's heart, records an electrocardiogram (EKG), and sends displacement signals to computer 14 via line 13a.

Figure 1B:
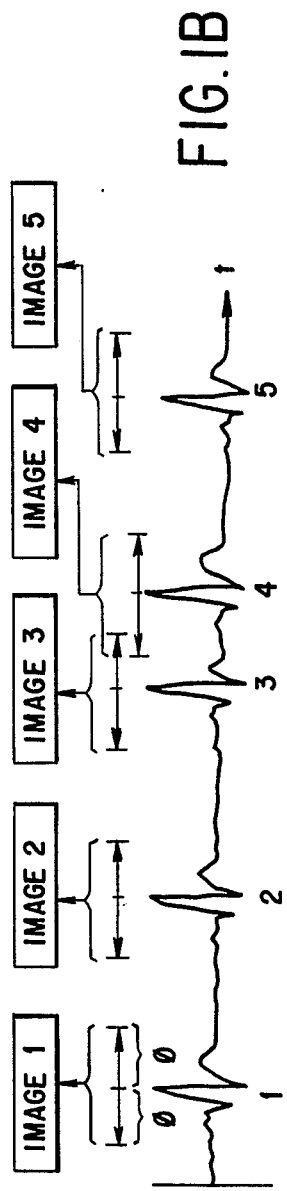
FIG. 1B is a schematic diagram illustrating the relation between several scan images and the patient's EKG shown in FIG. 1A.

FIG. 1B discloses the relation between the EKG of patient 10 and the portions of the projection data used to reconstruct each image in the first preferred embodiment.

Figure 2:
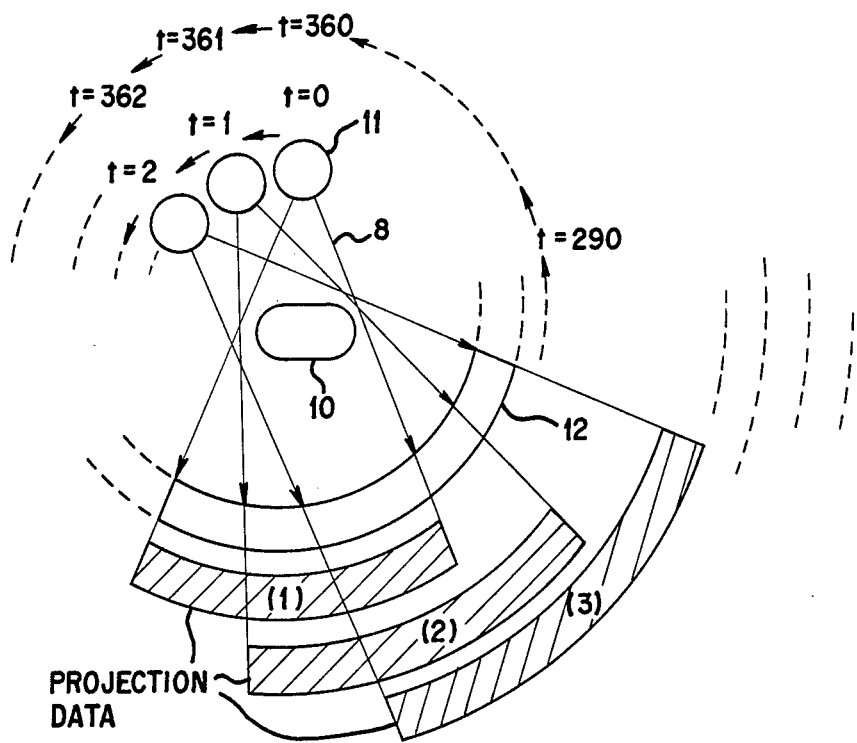
FIG. 2 is a schematic diagram illustrating projection data as related to rotation of the X-ray source.

FIG. 2 discloses projection data (1), (2), (3) . . . at each section t=0, 1, 2, etc. of the X-ray source 11. At the section t=0, projection data are detected by the part of the X-ray detector 12 located opposite the X-ray source 11. The X-ray source 11 rotates continuously around the patient 10 projecting an X-ray pattern in the form of fan beam 8. Rotation of the X-ray source 11 takes for example 0.47 sec from position t=0 to position t=360 and moves counterclockwise as shown in FIG. 2.

In FIG. 3, source position t describes the position of X-ray source 11 in one degree increments while it is rotating at constant speed around patient 10 as shown in FIG. 2, therefore t=0 and t=360 are the same position. Each projection number corresponds to the source position t of like number. Likewise the position of the X-ray detector 12 for projection data (1), (361), (721), etc. are the same location.

The EKG of patient 10 is sent from electrocardiograph 13 to computer 14 via line 13a (FIG. 1A). If the peak of an EKG R wave is defined as having a phase of 0, a change in phase of the EKG corresponds to each projection number. Memory means consisting of disk 19 stores the projection data, projection number, and phase $\phi$ of the EKG.

Figure 9:
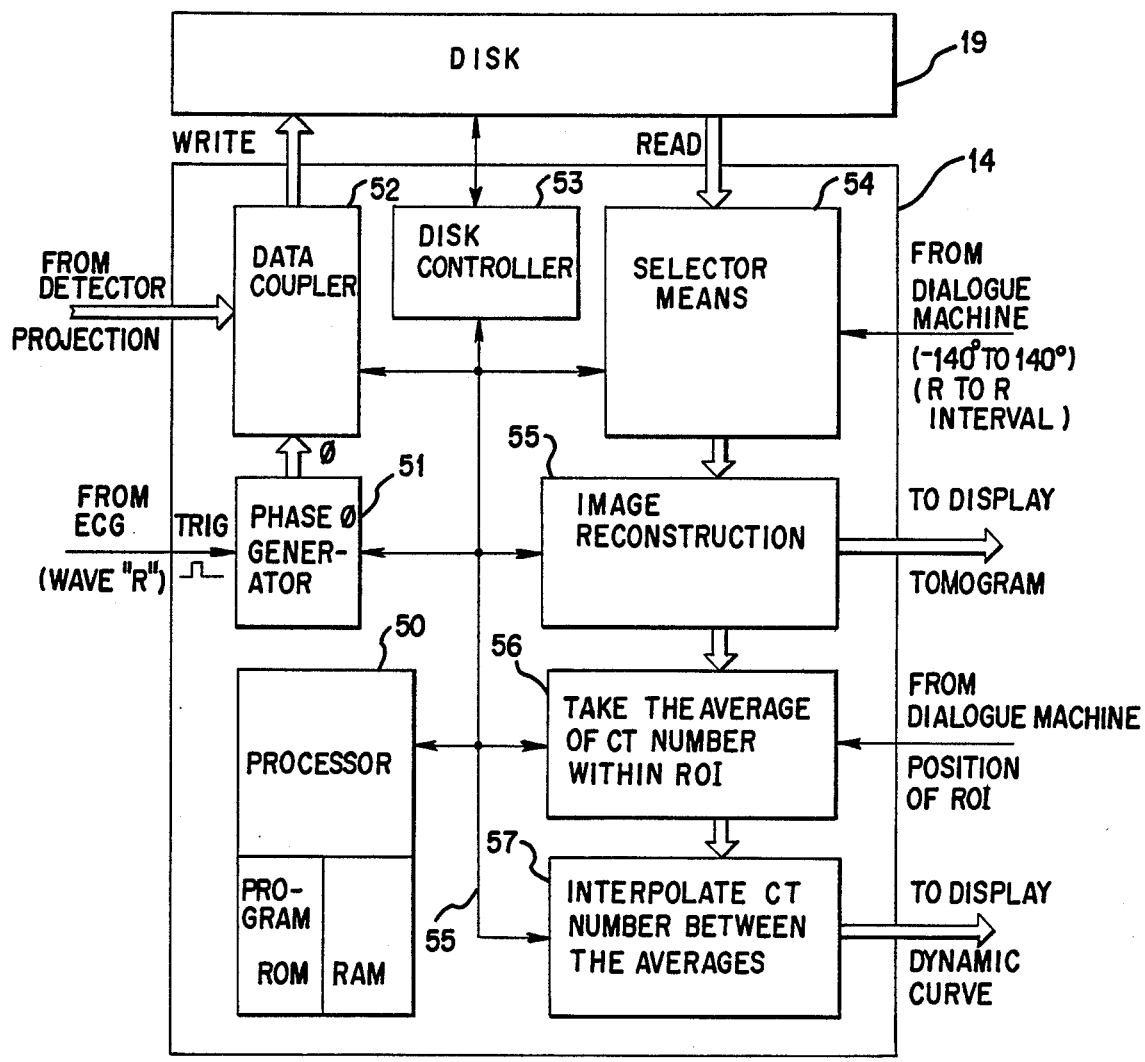
FIG. 9 is a schematic block diagram illustrating the computer used to process projection data and EKG signals to produce the images and dynamic curve of the present invention.

FIG. 9 shows the configuration of computer 14 of FIG. 1A. Phase generator 51 receives displacement signals from electrocardiograph 13 of FIG. 1A and provides them to data coupler 52 for storage on disk 19. The phase $\phi$ is triggered from the top of the EKG R wave because it is the most distinguishable signal from the electrocardiograph. Projection data from X-ray detector 12 of the scanning means is also sent to data coupler 52 and stored on disk 19 at the same time as the phase information from phase generator 51.

Figure 4:
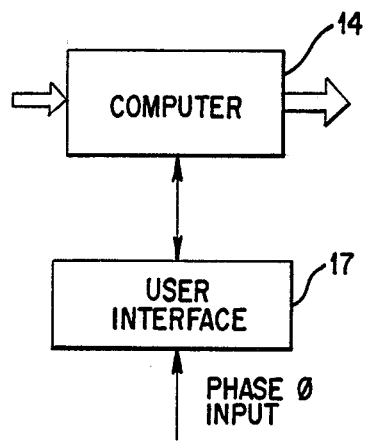
FIG. 4 is a schematic block diagram illustrating the user interface and computer.
Figures 5, 6:
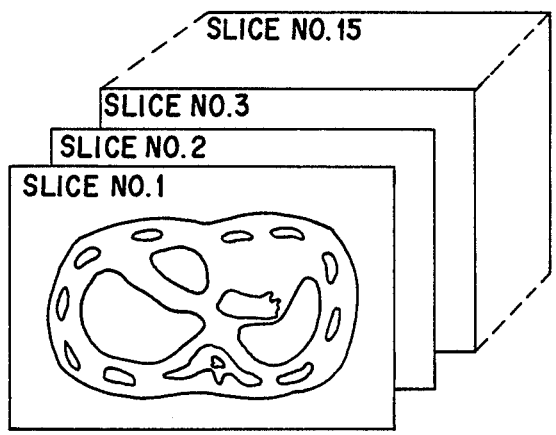
FIG. 5 is a table listing slice numbers, projection numbers, and phase.
FIG. 6 is a schematic diagram illustrating a series of scan images.

The system employs a first selecting means comprising a user interface 17 shown in FIG. 4 and selector means 54 of FIG. 9 within computer 14. A user inputs phase information through user interface 17, for example, $-140°$ to $+140°$ which is sent to selector means 54. These phases act as a window within which projection data will be collected in order to produce a CT image and characteristic curve of CT number versus time. Selector means 54 reads phase, projection data, and projection number from disk 19 corresponding to the phase selected on the user interface 17. In the first preferred embodiment, projection data are collected within the selected phase window, centered on a phase zero point, for example at the peak of the R wave as shown in FIG. 1B. Projection data corresponding to the selected phase are sent to image reconstruction means 55 of FIG. 9 which reconstructs a scan image of the patient. Examples of scan images are shown in FIG. 6. FIG. 5 shows consecutive projection numbers corresponding to each slice for the case in which the phase of the EKG R wave is selected on user interface 17 to be from $-140°$ to $+140°$. Projection numbers (2), (3), . . . , (282) are used to reconstruct slice number 1 as shown in the table of FIG. 5. These projection numbers, (2) to (282) are applicable only when the selected phase is from $-140°$ to $+140°$ as shown in the table of FIG. 3. Likewise the projection of other slices as shown in FIG. 6 are based on the projection numbers shown in the table of FIG. 5.

If the interval between EKG R waves is over $\phi_1$-$\phi_1 = 280°$ (slice No. 3 in FIG. 5), the reconstruction of slices may require the use of the same projection data, as in slices number 3 and number 4 which use projection data numbers (991), (992), . . . , (1002).

Figure 7:
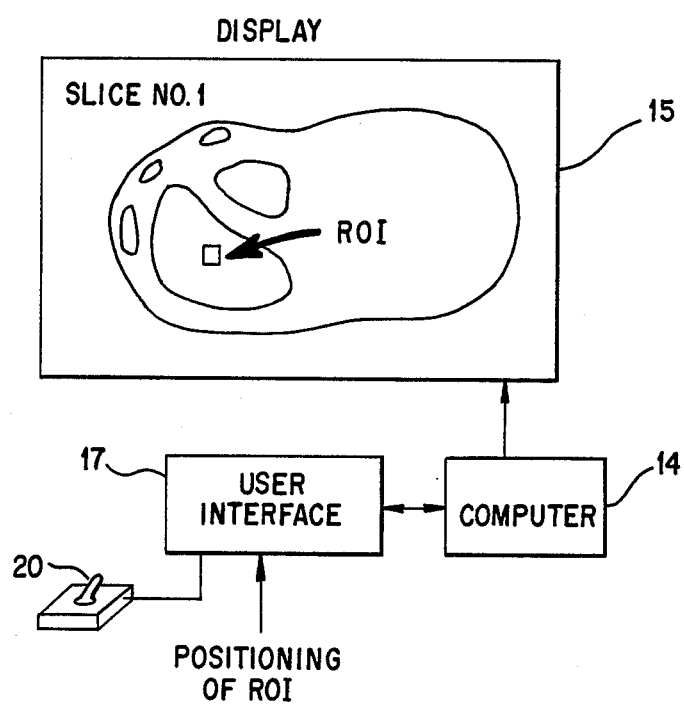
FIG. 7 is a schematic diagram illustrating the method of positioning the region of interest using the display and the user interface.

The image reconstructed by image construction block 55 of FIG. 9 is sent to the dynamic curve display means which consists of the CT number averaging circuit 56 and CT interpolating circuit 57 which also receives input from the second selecting means which consists of a region of interest position selected by the user through user interface 17. FIG. 7 shows an example region of interest (ROI) on slice number 1 of display 15. The operator may position the ROI using a joy stick 20 or a track ball connected to user interface 17.

The ROI generally contains several data elements, therefore the CT numbers are averaged within the ROI at block 56 of computer 14. At block 57, values are interpolated between the average CT numbers calculated at block 56 and the resulting curve is sent to display 15 to be expressed as the dynamic curve 16 of FIG. 8. Dynamic curve 16 plots the change in CT number or relative X-ray absorption in the region of interest selected by the operator over a period of time. The dynamic curve 16 of this invention provides a chain of accurate CT numbers therefore doctors can diagnose a patient 10 more correctly.

Figures 8, 10:
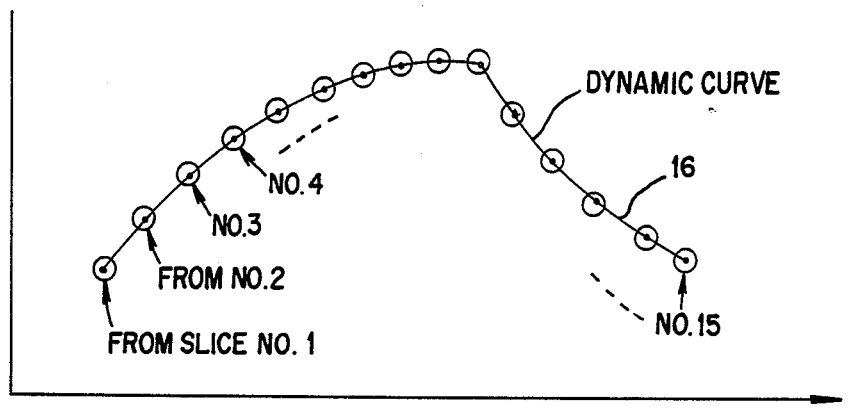
FIG. 8 is a schematic diagram illustrating the dynamic curve of averaged CT numbers versus time according to the present invention.
FIG. 10 is a table relating the slice numbers and projection numbers to the phase of the EKG R wave and R wave interval.
Figure 11A:
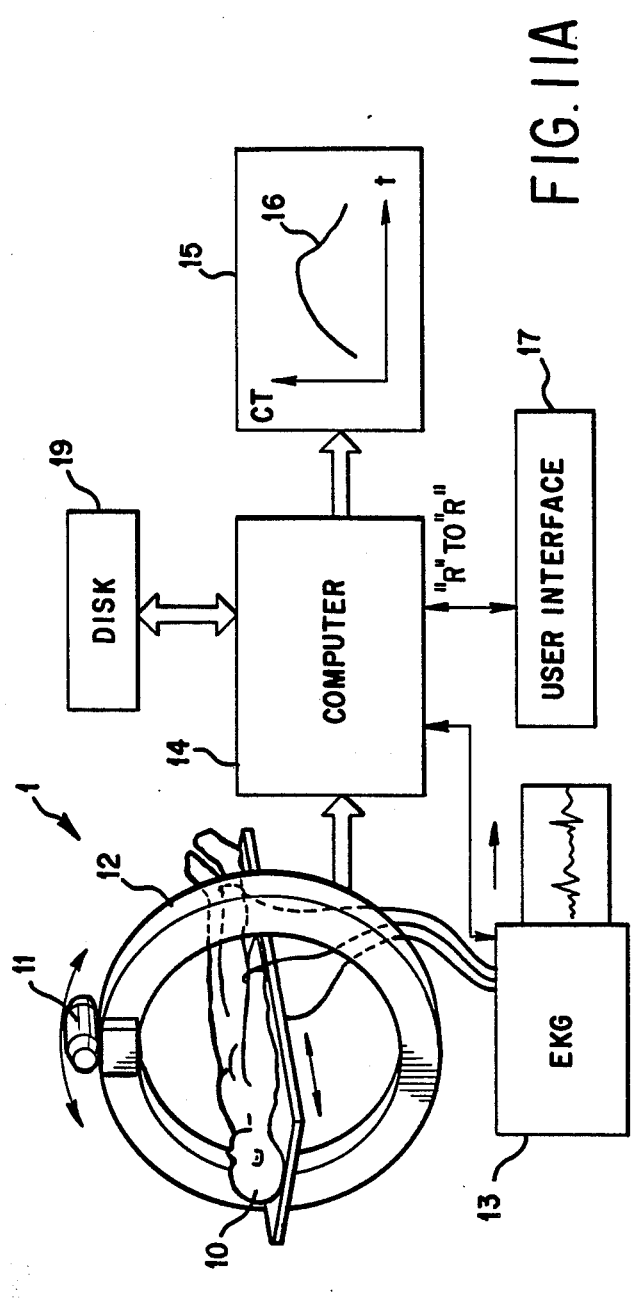
FIG. 11A is a schematic block diagram illustrating the dynamic scan system of the present invention.
Figure 11B:
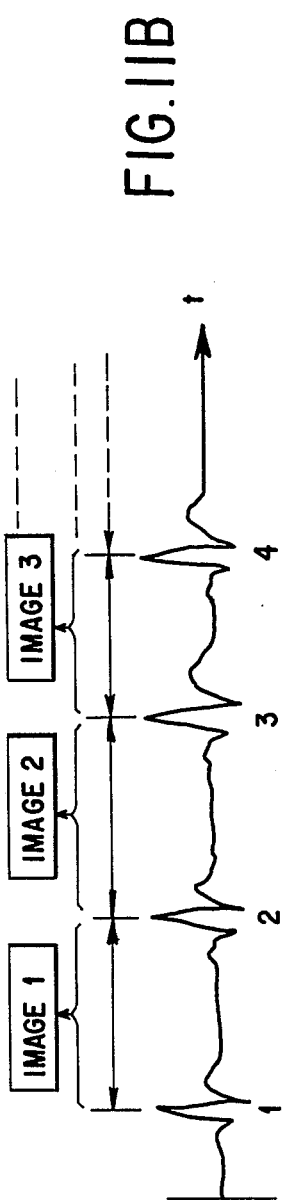
FIG. 11B is a schematic diagram illustrating the relation between several scan images and the patient's EKG shown in FIG. 11A.

In the second preferred embodiment shown in FIGS. 11A and 11B, the first specified phase where selection of projection data for each image starts is the peak of the EKG R wave and the second specified phase where selection of projection data stops is the peak of the next EKG R wave, therefore projection data used to generate each image is selected between the peaks of the R waves. The relationship between the slice number and the projection numbers is shown in the table of FIG. 10.

In determining whether to use the procedure of the first or the second preferred embodiment:

(1) When the projection data number is larger than that corresponding to one rotation of scanner 11:
  1. Among the data $P(\phi)$ from the angle of rotation $\alpha$ to $2\pi+\beta(\alpha<\beta)$, the projection data corresponding to $2\pi$ centered by $\pi+(\alpha+\beta)$ may be used.
  2. Where projection data are duplicated, the following weighing of both values may be used:

$$P(\phi)=P(\phi) \quad \alpha+\beta<\phi<2\pi+\alpha$$
$$P(\phi)*K+P(\phi+2)*(1-K) \quad \alpha<\phi<\beta$$

where the above coefficient K changes monotonically from 0 to 1 as shown in FIG. 9.

(2) When the projection data number is less than that resulting from one rotation of scanner 11:

When the projection data number is more than that of $180°=$X-ray fan beam fanning angle, reconstruction of the CT image is possible. For example, D. Darker in "Optical Short Scan Convolution Reconstruction," Medical Physics 9(2), Mar./Apr. 1982 describes that correct image reconstruction is possible under these conditions. The operation may therefore be executed by cutting out the required quantity ($\frac{1}{2}$ rotation angle=X-ray fan beam angle) of projection data centered by $(\phi_1+\phi_2)/2$, or (according to the description of the documents) when both are collected together from 180° opposite sides, the image is reconstructed by weighing the data so that their total sum becomes (and by usual convolution) back projection, so that the same weighting method may be applied to data exceeding $\frac{1}{2}$ the rotation angle=X-ray fan beam angle.

The method of this invention is not limited to dynamic scanning of the heart, but may also be applied to other portions of the body subject to cyclic displacement such as the lungs. In the case of dynamic scanning of the lungs, the phase synchronization can be made by replacing the EKG displacement signal by a respiration wave form.

This invention may also be applied using CT devices in which the direction of the X-ray tube reverses for each scan. This is a third generation X-ray CT device in which both the X-ray scanner and radiation detecting tube revolve, along with the cables handling the revolution of the radiation detecting tube. In this method, however, scanning speed is slower and two EKG R wave peaks may be detected within one revolution of the X-ray scanner, and the system may be made to reconstruct one cyclic image only because sufficient data may not be collected to create two separate images.

In this example the distortion of the heart image due to the heart beat is almost the same between all images which means that the images serves sufficiently well for a dynamic study of the cardiac muscles.

Moreover, even in devices in which continuous scanning is not used, for example in the case of Electron Beam Scanning described in Radiology of Skull and Brain, Volume 15 pages 4366 to 4369, high speed scanning is not repeated. The images produced by the projection data are obtained by adding and leveling scan data for acquiring high quality images with low noise. For this system, making an image by projection data having a specified width centered by a specified phase of varying period is very useful (by repeated scanning the scan time is substantially lengthened, therefore the concept of this invention is useful).

Further in magnetic resonance imaging, when an appropriate contrast medium is developed, and high-speed imaging is put to practical use with dynamic scanning, the concept of this invention can be applied.

As described above in detail and in accordance with the invention, a plurality of synchronized images of moving portions coincident in phase can be reconstructed, and in particular, synchronized image reconstruction devices optimum to the dynamic study can be developed.

What is claimed is:

1. A computed tomographic system for dynamic scanning of an object at cyclic displacements while exposing radiation energy to said object, comprising:
  (a) scanning means for generating projection data representing a measured characteristic of said object by scanning a portion of said object over a selected time period;
  (b) detecting means for generating displacement signals responsive to the cyclic displacement of said object during said time period;
  (c) memory means coupled to said scanning means and said detecting means for correlating with respect to time and storing said projection data and said displacement signals;
  (d) first selecting means coupled to said memory means for selecting specific phases of cyclic displacement in a region scanned within said object;
  (e) reconstructing means coupled to said first selecting means and said memory means for generating a plurality of images of said object from said projection data generated between said specific phases of said displacement signals, each of said images being generated from one displacement cycle of said object;
  (f) second selecting means coupled to said reconstructing means for selecting a region of interest in said region scanned within said object; and
  (g) dynamic curve display means coupled to said reconstructing means to average said measured characteristic within said region of interest for each of said images and to display said measured characteristic as a function of time.

2. The computed tomographic system of claim 1 wherein said first selecting means selects projection data collected at a fixed phase prior to and after the occurrence of a specified displacement signal.

3. The computed tomographic system of claim 1 wherein said first selecting means selects projection data starting at a first specified phase and ending at a second specified phase.

4. A computed tomographic system of claim 1 wherein said measured characteristic is relative x-ray absorption in said region of interest.

5. A computed tomographic method enabling dynamic scanning of an object at cyclic displacements while exposing radiation energy to said object, comprising:

(a) generating projection data representing a measured characteristic of said object by scanning a portion of said object over a selected time period;

(b) generating displacement signals responsive to the cyclic displacement of said object during said time period;

(c) correlating with respect to time and storing said projection data and said displacement signals;

(d) selecting specific phases of cyclic displacement in a region scanned of said object;

(e) generating a plurality of images of said object from said projection data generated between said specific phases of said displacement signals, each of said images being generated from one displacement cycle of said object;

(f) selecting a region of interest within said region scanned of said object; and (g) averaging said measured characteristic within said region of interest for each of said images and displaying said measured characteristic as a function of time.

6. The computed tomographic method of claim 5 wherein the step of selecting specific phases of cyclic displacement includes selecting projection data collected at a fixed phase prior to and after the occurrence of a specified displacement signal.

7. The computed tomographic method of claim 5 wherein said step of selecting a region of interest includes selecting projection data starting at a first specified phase and ending at a second specified phase.

8. A computed tomographic method of claim 5 wherein said measured characteristic is relative x-ray absorption in said region of interest.

* * * * *